United States Patent [19]
Eller et al.

[11] Patent Number: 5,900,508
[45] Date of Patent: May 4, 1999

[54] PREPARATION OF AMINES FROM OLEFINS OVER ZEOLITES OF THE TYPE PSH-3, MCM-22, SSZ-25 OR MIXTURES THEREOF

[75] Inventors: Karsten Eller, Ludwigshafen; Ulrich Müller, Neustadt; Rudolf Kummer, Frankenthal; Peter Stops, Altrip, all of Germany

[73] Assignee: BASF Aktiengesellschaft, Ludwigshafen, Germany

[21] Appl. No.: 08/683,227

[22] Filed: Jul. 18, 1996

[30] Foreign Application Priority Data

Jul. 20, 1995 [DE] Germany .................. 195 26 502

[51] Int. Cl.⁶ .................. C07C 209/60
[52] U.S. Cl. .................. 564/395; 564/408; 564/469; 564/485
[58] Field of Search .................. 564/395, 408, 564/469, 485

[56] References Cited

U.S. PATENT DOCUMENTS

| | | | |
|---|---|---|---|
| 4,307,250 | 12/1981 | Peterson et al. | 564/445 |
| 4,375,002 | 2/1983 | Peterson | 564/445 |
| 4,536,602 | 8/1985 | Deeba | 564/485 |
| 4,826,667 | 5/1989 | Zones et al. | 423/277 |
| 4,929,758 | 5/1990 | Taglieber et al. | 564/485 |
| 5,304,681 | 4/1994 | Knifton et al. | 564/485 |

FOREIGN PATENT DOCUMENTS

| | | |
|---|---|---|
| 0101921 | 3/1984 | European Pat. Off. . |
| 0132736 | 2/1985 | European Pat. Off. . |
| 0133938 | 3/1985 | European Pat. Off. . |
| 0 305 564 | 3/1989 | European Pat. Off. . |
| A 431 451 | 6/1991 | European Pat. Off. . |
| 42 06 992 | 9/1993 | Germany . |

OTHER PUBLICATIONS

Jean–Jacques Brunet, Denis Neibecker & Francine Niedercorn, "Functionalisation of Alkenes: Catalytic Amination of Monoolefins", *Journal of Molecular Catalysis*, 49, (1989), 235–259.

*Primary Examiner*—José Q. Dees
*Assistant Examiner*—Barbara Badio
*Attorney, Agent, or Firm*—John H. Shurtleff

[57] ABSTRACT

A process for the preparation of amines by reacting an olefin with ammonia or a primary or secondary amine at a temperature of from 200 to 350° C. and a pressure of from 100 to 300 bar in the presence of at least one zeolite having the specific structure type PSH-3, MCM-22 or SSZ-25, as identified by X-ray diffractogram, or mixtures of these zeolites. These specific catalysts are broadly identified as alumina zeolites and may be modified by ion exchange, doping with other metals, by dealumination to remove or replace the alumina content and by other well known after treatments such as calcination, acid-treatment and the like. Monoolefins are preferred reactants but di- and polyolefins also can be reacted with relatively high selectivity and less tendency toward polymerization.

13 Claims, No Drawings

PREPARATION OF AMINES FROM OLEFINS OVER ZEOLITES OF THE TYPE PSH-3, MCM-22, SSZ-25 OR MIXTURES THEREOF

DESCRIPTION

The present invention relates to a process for preparing amines by reacting ammonia or primary or secondary amines with olefins at elevated temperatures and pressures in the presence of zeolites of the type PSH-3, MCM-22, SSZ-25 or mixtures thereof.

The methods for aminating olefins are reviewed in Functionalisation of Alkenes: Catalytic Amination of Monoolefins, J. J. Brunet et al. J. Mol.Catal., 49 (1989), 235–259.

There are basically two mechanisms of catalysis. The olefin is coordinated via a metal complex. This activated species can be attacked by the nucleophilic amine to form a more highly aminated product. The amine can be chemisorbed on acid centers or on metal centers (via metal amides) and reacted with the olefin in this activated state.

Zeolites are suitable catalysts. They have a large number of catalytically active centers coupled with a large surface area. The zeolites which have been described differ in type and in the aftertreatment (eg. thermal treatment, dealumination, acid treatment, metal ion exchange, etc.). Examples may be found in U.S. Pat. No. 4,375,002, U.S. Pat. No. 4,536,602, EP-A-305 564, EP-A-101 921, DE-A-42 06 992.

EP-A-133 938, EP-A-431 451 and EP-A-132 736 disclose processes wherein borosilicate, gallium silicate, aluminosilicate and iron silicate zeolites are used for preparing amines from olefins and mention the possibility of doping these zeolites with alkali, alkaline earth and transition metals.

CA-A-2 092 964 discloses a process for preparing amines from olefins using BETA zeolites, defined as crystalline aluminosilicates of certain composition with a pore size of more than 5 Å. Preference is given to using metal- or halogen-modified BETA zeolites.

All processes for synthesizing amines from olefins over these catalysts have a low amine yield or a low space-time yield or lead to rapid deactivation of the catalysts.

It is an object of the present invention to remedy these disadvantages.

We have found that this object is achieved by a novel and improved process for preparing amines of the general formula I

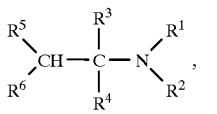

where $R^1, R^2, R^3, R^4, R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ are each $C_{21}$–$C_{200}$-alkyl or $C_{21}$–$C_{200}$-alkenyl or together a $C_2$–$C_{12}$-alkylene dichain, by reacting olefins of the general formula II

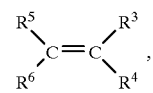

where $R^3$, $R^4$, $R^5$ and $R^6$ are each as defined above, with ammonia or primary or secondary amines of the general formula III

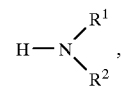

where $R^1$ and $R^2$ are each as defined above, at temperatures from 200 to 350° C. and pressures from 100 to 300 bar in the presence of a heterogeneous catalyst, which comprises using a heterogeneous catalyst comprising zeolites of the type PSH-3, MCM-22 or SSZ-25 or mixtures thereof.

The process of the present invention can be carried out as follows:

The olefin II and ammonia or the primary or secondary amine III can be reacted at temperatures from 200 to 350° C., preferably from 220 to 330° C., particularly preferably from 230 to 320° C., and pressures from 100 to 300 bar, preferably from 120 to 300 bar, particularly preferably from 140 to 290 bar, in the presence of zeolites of the type PSH-3, MCM-22, SSZ-25 or mixtures thereof as catalyst, for example in a pressure reactor, and preferably the amine obtained is separated off and the unconverted feed materials are recycled.

The present process is notable for a very good yield combined with high selectivity and a high space-time yield. In addition, the deactivation of the catalyst is suppressed.

The process of the present invention is notable for the fact that even a small excess of ammonia or amine will produce a high selectivity in respect of the desired reaction product and will inhibit the dimerization and/or oligomerization of the olefin used.

In one embodiment of this process, ammonia and/or amines III are fed together with the olefin II in a mixture in a molar ratio of from 1:1 to 5:1 into a fixed-bed reactor and reacted therein at a pressure of from 100 to 300 bar and a temperature from 200 to 350° C. in the gas phase or in the supercritical state.

The desired product can be obtained from the reaction effluent with the aid of known methods, for example distillation or extraction, and if necessary brought to the desired purity by means of further separating operations. The unconverted feed materials are generally preferably recycled into the reactor.

It is possible to use monounsaturated or polyunsaturated olefins II, in particular those having from 2 to 10 carbon atoms, or mixtures thereof and polyolefins as starting materials. Owing to the less pronounced tendency to polymerize, monoolefins are more suitable than di- and polyolefins, but the latter can be reacted just as selectively by means of higher ammonia or amine excesses. The position of the equilibrium and hence the conversion to the desired amine is very highly dependent on the reaction pressure used. High pressure favors the addition product, but the range of up to 300 bar will generally represent the optimum for technical and commercial reasons. The selectivity of the reaction is influenced not only by variables such as ammonia/amine excess and catalyst but also to a high degree by the temperature. It is true that the reaction rate of the addition reaction increases strongly with increasing temperature, but competing cracking and recombination reactions of the olefin are promoted at the same time. In addition, a temperature increase is not advantageous from a thermodynamic aspect. The position of the temperature optimum as regards conversion and selectivity is dependent on the constitution of the olefin, of the amine used and of the catalyst and is usually within the range from 200 to 350° C.

Suitable catalysts for the amination of olefins are zeolites of the type PSH-3, MCM-22, SSZ-25 or mixtures thereof, preferably MCM-22 zeolites known for example from Stud. Surf. Sci. Catal., 84 (1994), 331–338.

U.S. Pat. No. 4,954,325 discloses a zeolite of the designation MCM-22 whose pore distribution lies between the pore distribution of a ZSM-12 and the pore distribution of a BETA zeolite. U.S. Pat. No. 4,439,409 discloses such an MCM-22 zeolite under the name of PSH-3, and EP-A-231 019 discloses an MCM-22 zeolite under the name SSZ-25 with a very similar X-ray diffractogram.

The zeolites MCM-22, PSH-3 and SSZ-25 of the present invention can be molded as such or else using a binder in a ratio of from 98:2 to 40:60% by weight into extrudates or tablets. Suitable binders include various aluminas, preferably boehmite, amorphous aluminosilicates having an $SiO_2/Al_2O_3$ ratio of from 25:75 to 95:5, silica, preferably finely divided $SiO_2$, mixtures of finely divided $SiO_2$ and finely divided $Al_2O_3$, finely divided $TiO_2$, and also clays. After molding, the extrudates or tablets are advantageously dried at 110° C. for 16 h and calcined at from 200 to 500° C. for from 2 to 16 h, it also being possible for the calcination to be carried out directly in the amination reactor.

To enhance the selectivity, the on-stream time and the number of possible regenerations, various modifications can be made to the zeolite catalysts MCM-22, PSH-3 and SSZ-25 of the present invention.

One way of modifying the catalysts comprises ion-exchanging or doping the molded or unmolded zeolites with alkali metals such as Na and K, alkaline earth metals such as Ca and Mg, earth metals such as Tl, transition metals such as, for example, Ti, Zr, Mn, Fe, Mo, Cu, Zn and Cr, noble metals and/or rare earth metals such as, for example, La, Ce and Y.

An advantageous embodiment comprises presenting the molded zeolites MCM-22, PSH-3 and SSZ-25 of the present invention in a flow tube and passing for example a halide, an acetate, an oxalate, a citrate or a nitrate of the above-described metals thereover in dissolved form at from 20 to 100° C. Such an ion exchange can be carried out for example on the hydrogen, ammonium or alkali metal form of the zeolites MCM-22, PSH-3 and SSZ-25 of the present invention.

A further way of applying metal to the zeolites MCM-22, PSH-3 and SSZ-25 of the present invention comprises impregnating the material for example with a halide, an acetate, an oxalate, a citrate, a nitrate or an oxide of the above-described metals in aqueous or alcoholic solution.

Both an ion exchange and an impregnation may be followed by drying, alternatively by a further calcination. In the case of metal-doped zeolites of the type MCM-22, PSH-3 and SSZ-25, an aftertreatment with hydrogen and/or with water vapor can be advantageous.

A further way of achieving modification comprises subjecting the zeolites MCM-22, PSH-3 and SSZ-25 of the present invention—molded or unmolded—to a treatment with acids, such as hydrochloric acid (HCl), hydrofluoric acid (HF), sulfuric acid ($H_2SO_4$), phosphoric acid ($H_3PO_4$) or oxalic acid ($HO_2C-CO_2H$).

A particular embodiment comprises refluxing the zeolites MCM-22, PSH-3 and SSZ-25 of the present invention for from 1 to 100 hours with one of the aforementioned acids at from 0.001N to 2N, preferably from 0.05 to 0.5N, prior to molding. Collection by filtration and washing is generally followed by drying at from 100 to 160° C. and calcination at from 200 to 600° C. A further particular embodiment comprises an acid treatment of the zeolites MCM-22, PSH-3 and SSZ-25 of the present invention after their molding with binder. Here the zeolite of the present invention is generally treated with an acid from 3 to 25% in strength, in particular from 12 to 20% in strength, at from 60 to 80° C. for from 1 to 3 hours, then washed, dried at from 100 to 160° C. and calcined at from 200 to 600° C.

Another way of achieving modification is by exchange with ammonium salts, for example with $NH_4Cl$, or with mono-, di- or polyamines. Here the binder-molded zeolite is generally exchanged at from 60 to 80° C. with a from 10 to 25% in strength, preferably 20% in strength, $NH_4Cl$ solution in a continuous manner for 2 h in a zeolite/ammonium chloride solution of 1:15 by weight and thereafter dried at from 100 to 120° C.

A further possible modification of the zeolites of this invention comprises a dealumination in which some of the aluminum atoms are replaced by silicon or the zeolites are diminished in their aluminum content by a hydrothermal treatment, for example. A hydrothermal dealumination is advantageously followed by an extraction with acids or complexing agents to remove nonlattice aluminum formed. The replacement of aluminum by silicon can be effected with the aid of $(NH_4)_2SiF_6$ or $SiCl_4$, for example. Examples of dealuminations of Y-zeolites are found in Corma et al., Stud. Surf. Catal. 37 (1987), 495–503.

The catalysts can be used for the amination of olefins as extrudates having diameters from, for example, 1 to 4 mm or as tablets with diameters from, for example, 3 to 5 mm.

The catalyst, molded into extrudates for example, can be made to yield a fluidizable material from 0.1 to 0.8 mm in size by grinding and sieving.

The substituents $R^1$, $R^2$, $R^3$, $R^4$, $R^5$ and $R^6$ in the compounds I, II and III have the following meanings:

$R^1, R^2, R^3, R^4, R^5, R^6$ hydrogen, $C_1–C_{20}$-alkyl, preferably $C_1–C_{12}$-alkyl, particularly preferably $C_1–C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2–C_{20}$-alkenyl, preferably $C_2–C_{12}$-alkenyl, particularly preferably $C_2–C_8$-alkenyl such as vinyl and allyl, $C_2–C_{20}$-alkynyl, preferably $C_2–C_8$-alkynyl, in partiucular $C_2H$ and propargyl, $C_3–C_{20}$-cycloalkyl, preferably $C_3–C_{12}$-cycloalkyl, particularly preferably $C_5–C_8$-cycloalkyl such as cyclopentyl, cyclohexyl, cycloheptyl and cyclooctyl, $C_4–C_{20}$-alkylcycloalkyl, preferably $C_4–C_{12}$-alkylcycloalkyl, particularly preferably $C_5–C_{10}$-alkylcycloalkyl, $C_4–C_{20}$-cycloalkylalkyl, preferably $C_4–C_{12}$-cycloalkylalkyl, particularly preferably $C_5–C_{10}$-cycloalkylalkyl, aryl such as phenyl, 1-naphthyl and 2-naphthyl, preferably phenyl, $C_7–C_{20}$-alkylaryl, preferably $C_7–C_{16}$-alkylaryl, preferably $C_7–C_{12}$-alkylphenyl such as 2-methylphenyl, 3-methylphenyl, 4-methylphenyl, 2-ethylphenyl, 3-ethylphenyl and 4-ethylphenyl, $C_7$–$C_{20}$-aralkyl, preferably $C_7$–$C_{16}$-aralkyl, preferably $C_7$–$C_{12}$-phenalkyl such as phenylmethyl, 1-phenylethyl, 2-phenylethyl, $R^1$ and $R^2$
together a saturated or unsaturated $C_3$–$C_9$-alkylene dichain, preferably —$(CH_2)_4$—, —$(CH_2)_5$—, —$(CH_2)_7$— and —CH=CH—CH=CH—, $R^3$ or $R^5$
$C_{21}$–$C_{200}$-alkyl, preferably $C_{40}$–$C_{200}$-alkyl, such as polybutyl, polyisobutyl, polypropyl, polyisopropyl und polyethyl, particularly preferably polybutyl and polyisobutyl,
$C_{21}$–$C_{200}$-alkenyl, preferably $C_{40}$–$C_{200}$-alkenyl, particularly preferably $C_{70}$–$C_{170}$-alkenyl, $R^3$ and $R^5$
together a $C_2$–$C_{12}$-alkylene dichain, preferably a $C_3$–$C_8$-alkylene dichain, particularly preferably —$(CH_2)_3$—, —$(CH_2)_4$—, —$(CH_2)_5$—, —$(CH_2)_6$— and —$(CH_2)_7$—, in particular —$(CH_2)_3$— and —$(CH_2)_4$—.

EXAMPLES

Catalyst Synthesis 30 g of MCM-22 were admixed with 20 g of boehmite and 1 g of formic acid, compacted in a kneader and kneaded for 45 minutes with the addition of 52 ml of water. 2 mm extrudates were produced in an extruder under a molding pressure of 40 bar, dried at 120° C. for 16 h and then calcined at 500° C. for 16 h.

Amination Examples

The runs were carried out in a tubular reactor (6 mm internal diameter) under isothermal conditions at from 260° C. to 300° C. and a pressure of 280 bar using a mixture of isobutene and ammonia in a molar ratio of 1:1.5. The reaction products were analyzed by gas chromatography.

The results are summarized in Table 1.

TABLE 1 tert-butylamine ($NH_3$ : $C_4H_8$ = 1.5)

| Pressure [bar] | Temperature [°C.] | tert-Butylamine yield [% by weight] | | | Weight per liter [kg/l] |
| --- | --- | --- | --- | --- | --- |
| | | WHSV 0.7 [g/g · h] | WHSV 1.5 [g/g · h] | WHSV 3 [g/g · h] | |
| 280 | 260 | 18.81 | | | 0.43 |
| 280 | 270 | 20.50 | 17.34 | 13.26 | 0.43 |
| 280 | 280 | 17.89 | 16.99 | 14.60 | 0.43 |
| 280 | 300 | | | 11.89 | 0.43 |

We claim:

1. A process for preparing an amine which comprises reacting an olefin with ammonia or a primary or secondary amine at an elevated temperature of from 200 to 350° C. and under a pressure of from 100 to 300 bar in the presence of a heterogeneous zeolite catalyst having the specific structure type PSH-3, MCM-22 or SSZ-25, as identified by X-ray diffractogram, or mixtures of these zeolites.

2. A process as claimed in claim 1 wherein the amine product is separated off and the unconverted reactants are recycled to the reaction in the presence of said catalyst.

3. A process as claimed in claim 1 for preparing amines of the formula I

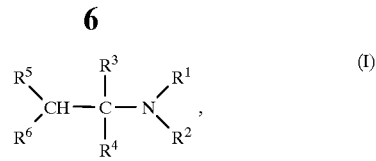

where $R^1, R^2, R^3, R^4, R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ are each $C_{21}$–$C_{200}$-alkyl or $C_{21}$–$C_{200}$-alkenyl or together a $C_2$–$C_{12}$-alkylene dichain, by reacting olefins of the formula II

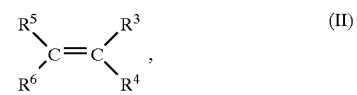

where $R^3$, $R^4$, $R^5$ and $R^6$ are each as defined above, with ammonia or primary or secondary amines of the general formula III

where $R^1$ and $R^2$ are each as defined above.

4. A process as claimed in claim 3, wherein the product amine I is separated off and the unconverted feed materials II and III are recycled.

5. A process as claimed in claim 1 wherein the olefin reactant is selected from the group consisting of isobutene, diisobutene, cyclopentene, cyclohexene, polyisobutene and mixtures thereof.

6. A process as claimed in claim 1 wherein said zeolite catalyst is used in its H-form.

7. A process as claimed in claim 1 wherein said zeolite catalyst has been treated with an acid selected from the group consisting of hydrochloric acid, hydrofluoric acid, sulfuric acid, phosphoric acid, oxalic acid and mixtures thereof.

8. A process as claimed in claim 1 wherein said zeolite catalyst has been doped with one or more transition metals.

9. A process as claimed in claim 1 wherein said zeolite catalyst has been doped with one or more rare earth elements.

10. A process as claimed in claim 1 wherein said zeolite catalyst has been modified by exchange with an ammonium salt to place it in the ammonium form.

11. A process as claimed in claim 1 wherein said zeolite catalyst has been doped with one or more elements selected from the group consisting of alkali metals, alkaline earth metals or earth metals.

12. A process as claimed in claim 1 wherein said heterogeneous zeolite catalyst is molded with a binder and calcined at a temperature from 200 to 600° C.

13. A process as claimed in claim 1 wherein said heterogeneous zeolite catalyst is partially dealuminated, optionally with partial replacement by silicon.

* * * * *